(12) United States Patent
Hanusse

(10) Patent No.: US 8,731,647 B2
(45) Date of Patent: May 20, 2014

(54) METHOD AND SYSTEM FOR ANALYZING THE CARDIAC ACTIVITY OF A PATIENT AND USES THEREOF

(75) Inventor: Patrick Hanusse, Pessac (FR)

(73) Assignee: Centre National de la Recherche Scientifique (C.N.R.S), Paris (FR)

( * ) Notice: Subject to any disclaimer, the term of this patent is extended or adjusted under 35 U.S.C. 154(b) by 0 days.

(21) Appl. No.: 13/640,708

(22) PCT Filed: Apr. 12, 2011

(86) PCT No.: PCT/FR2011/050828
§ 371 (c)(1),
(2), (4) Date: Nov. 8, 2012

(87) PCT Pub. No.: WO2011/128571
PCT Pub. Date: Oct. 20, 2011

(65) Prior Publication Data
US 2013/0053715 A1 Feb. 28, 2013

(30) Foreign Application Priority Data

Apr. 13, 2010 (FR) ...................................... 10 52788

(51) Int. Cl.
*A61B 5/04* (2006.01)
(52) U.S. Cl.
USPC ........................................................ 600/510
(58) Field of Classification Search
USPC ........................................................ 600/510
See application file for complete search history.

(56) References Cited

U.S. PATENT DOCUMENTS 5,020,540 A * 6/1991 Chamoun ..................... 600/509

FOREIGN PATENT DOCUMENTS

FR 2955187 A1 7/2011

OTHER PUBLICATIONS

Centre De Recherche Paul Pascal (CRPP) Oct. 9, 2005 Presentation entitled "Presentation de l'equipe Structures et dynamiques non-lineaires." (XP007917496).

(Continued)

*Primary Examiner* — Robert N Wieland
(74) *Attorney, Agent, or Firm* — Knobbe, Martens, Olson & Bear, LLP

(57) ABSTRACT

This method for analyzing the cardiac activity of a patient are comprises the steps for acquiring (20) at least one cardiac said electric signal comprising at least one elementary signal corresponding to a heart beat, for extracting (29) from said elementary signal, at least one elementary wave, the general shape of which may be expressed by $x(t)=x_0+x_1 \cos(\Phi(t))$, wherein $\Phi(t)$ is the phase of said elementary wave, and for analyzing (30) said elementary wave, comprising the steps for determining an expression of a phase equation $$F(\Phi) = \frac{d\Phi}{dt}$$

Figure 1:
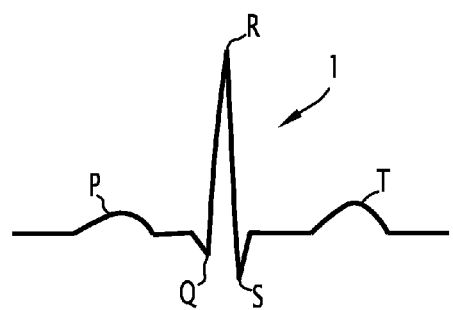

of said elementary wave and determining an expression of the phase $\Phi(t)$ of said elementary wave as a functions of parameters measuring the anharmonicity of said elementary wave and its morphology, from $p\cos_n$ and $p\sin_n$ functions defined by:

$$p\cos_n(t,r) = \sum_{k=1}^{\infty} \cos(kt)\frac{r^k}{k^n} \text{ and } p\sin_n(t,r) = \sum_{k=1}^{\infty} \sin(kt)\frac{r^k}{k^n}.$$

7 Claims, 1 Drawing Sheet

(56) References Cited

OTHER PUBLICATIONS

Centre De Recherche Paul Pascal (CRPP) listing of presentation by Hanusse, P. on Oct. 8, 2008 "Phénomènes périodiques non-linéaires: Théorie de l'anharmonicité" (see p. 20). (XP007917497).

Hanusse, P. Mar. 10-12, 2010 "Théorie de l'anharmonicité des phénomènes périodiques non-linéaires" Résumé d'un exposé soumis pour la 13e rencontre du Non-Linéaire. (XP055012353).

Hanusse, P. 2011 "A novel approach to anharmonicity for a wealth of applications in nonlinear science technologies" *International Conference on Applications in Nonlinear Dynamics—ICAND 2010* 1339: 303-308. (XP055012260).

Institut Henri Poincare 2010 Résumés des exposés de la 13e Rencontre du Non-Linéaire, located on the internet at: nonlineaire.univ-lille1.fr/SNL/media/2010/resumes/ResumesRNL2010sel.pdf, (see p. 24). (XP055012351).

Institut Henri Poincare 2010 Résumés des exposés de la 13e Rencontre du Non-Linéaire, located on the internet at: nonlineaire.univ-lille1.fr/SNL/media/2010/resumes/ResumesRNL2010sel.pdf, (see Table des matieres). (XP055012352).

Kraskov, A. et al. 2004 "Extracting phases from aperiodic signals" located on the internet at: arxiv.org/pdf/cond-mat/0409382.pdf. (XP002627501).

Science Non-Lineaire 2010 "Index of /SNL/media/2010/resumes" located on the Serveur du site Internet de la 13e Rencontre du Non Lineaire, Mar. 10-12, 2010, Paris, France, located on the internet at: nonlineaire.univ-lille1.fr/SNL/media/2010/resumes. (XP055012387).

Science Non-Lineaire 2010 "Programme de la 13e Rencontre du Non-Lineaire" located on the Serveur du site Internet de la 13e Rencontre du Non Lineaire, Mar. 10-12, 2010, Paris, France, located on the internet at: nonlineaire.univ-lille1.fr/SNL/media/2010/programme/ProgrammeRNL2010.pdf. (XP055012355).

\* cited by examiner

METHOD AND SYSTEM FOR ANALYZING THE CARDIAC ACTIVITY OF A PATIENT AND USES THEREOF

The present invention relates to a method for analyzing the cardiac activity of a patient, comprising the steps for acquiring at least one cardiac electric signal, comprising at least one elementary signal corresponding to a heart beat, for extracting from said elementary signal at least one elementary wave, the general shape of which may be expressed by $x(t)=x_0+x_1 \cos(\Phi(t))$, wherein $\Phi(t)$ is the phase of said elementary wave, and for analyzing the said elementary wave, and to a corresponding analysis system.

It also relates to the applications of the latter to a heart stimulator and defibrillator.

In particular, it applies to the field of electrocardiography and to the analysis of the electrocardiograms.

The electrocardiogram is the graphical representation of heart activity, recorded by electrodes are placed at the surface of the body. In conventional electrocardiography, the heart's electric activity is studied by recording from a series of 12 leads, each leader corresponding to a voltage line joining two electrodes placed in two determined points of the surface of the body and between which are recorded potential differences. The thereby recorded curves represents the depolarization and repolarization of the atrial and ventricular muscles, which are repeated quasi-periodically at each cardiac cycle.

Each of the leads corresponds to a signal, subsequently called an ECG signal, comprising a succession of elementary signals, or PQRST complex, each ring presenting a complete cardiac cycle, being repeated at regular time intervals.

Such an elementary signal consists of a succession of either positive or negative elementary waves, on either side of a so-called <<isoelectric>> line corresponding to a resting heart. These positive or negative waves result from well-defined physiological processes, and are generally identified by the standardized labels P, Q, R, S and T. The wave P is generated during depolarization of the atrium, the QRS complex represents the depolarization of the ventricle and the T wave is generated during repolarization of this ventricle.

By analyzing the elementary signals and their variability, possible heart abnormalities may be detected. This analysis, which was conducted for a long time as simply by reading the paper plot of the signal, comprises the measurement of the heart rate, generally determined from the interval between two R waves, the measurement of amplitudes and durations as well as examination of the morphology of the P wave, of the QRS complex, of the T wave, of the PR interval, of the ST segment, and of the QT interval.

Signal processing techniques henceforth give the possibility of conducting an automatic analysis of the ECG signal, and provide synthetic results from which the physician may make a diagnosis. This automatic analysis is generally carried out by breaking down the ECG signal into elementary signals, each comprising PQRST complex, breaking down each of these elementary signals, into elementary waves (P, Q, R, S and T waves), and then analyzing each elementary wave and characterizing these waves by several parameters. A synthesis of these parameters and of their time-dependent change is finally carried out, and gives the possibility of detecting possible abnormalities.

Many methods for analyzing and characterizing an ECG signal have been proposed. In particular, frequency analysis of the signal allows this signal to be described in Fourier space. The Fourier decomposition actually consists in breaking down a periodic signal of frequency f into an infinite sum of sinusoidal functions with frequencies which are multiples of F, weighted with Fourier coefficients. These Fourier coefficients, which form a coding of the analyzed signal, are characteristics parameters of this signal. In practice, the number of retained Fourier coefficients is limited and only the first terms of the Fourier decomposition are kept. These terms should however be in a sufficient number so that the signal synthesized from the coding is as close as possible to the original signal.

Now, the ECG signal is a strongly anharmonic signal, i.e. a non-linear signal, and the Fourier decomposition of this signal requires that a large number of coefficients be retained, coefficients to which it is difficult to give a physical meaning. Further, this decomposition, if it allows a description of the distribution of the frequency components of the signal, by no means gives any information on the instants when the latter occur, and does not allow characterization of the different waves (P wave, QRS complex, T wave . . . ) of the signal and their shape.

This drawback may be overcome by modeling the obtained ECG signal by breaking down this signal into a sum of wavelets or Gaussian waves. However, this method also requires the determination of a very large number of parameters in order that the modeling be of sufficient quality. Moreover, P and T waves, which may be assimilated with difficulty to Gaussian waves, are generally poorly modeled.

Moreover, from document <<A dynamical model for generating electrocardiogram signals>> (McSharry et al., IEEE Transactions on Biomedical Engineering 50(3): 289-294, March 2003), a method for modeling ECG signals is known, allowing ECG signals to be generated from statistical parameters such as the average and the standard deviation of the heart rate, and from morphology parameters notably relating to the morphology of the PQRST complex.

However, this method does not allow direct analysis of an ECG signal. Further, it is based on complex calculations, requiring that complete numerical integration be carried out for each fixed set of parameters.

Therefore, the object of the invention is to allow analysis of the wave shapes of cardiac activity signals, by means of a small number of parameters, relatively to the number of parameters required for the analysis via a Fourier series or for the decomposition into wavelets or Gaussian waves, said parameters bearing a physical meaning and forming a simple and explicit signature of the shape of the signals.

For this purpose, the object of the invention is an analysis method of the aforementioned type, characterized in that the analysis of said elementary wave comprises the following steps:

determining an expression of a phase equation $$F(\Phi) = \frac{d\Phi}{dt}$$

of said elementary wave; and determining an expression of the phase $\Phi(t)$ of said elementary wave depending on parameters measuring the anharmonicity of said elementary wave and its morphology, from $p \cos_n$ and $p \sin_n$ functions defined by:

$$p\cos_n(t, r) = \sum_{k=1}^{\infty} \cos(kt)\frac{r^k}{k^n} \text{ and } p\sin_n(t, r) = \sum_{k=1}^{\infty} \sin(kt)\frac{r^k}{k^n}.$$

The method according to the invention also includes the following characteristics, taken separately or as a combination:

the phase equation is expressed as:

$$\frac{d\Phi}{dt} = \frac{1 + r^2 + 2r\cos(\Phi)}{1 - r^2},$$

wherein r, varying in [0,1], is a parameter measuring the anharmonicity of said elementary wave;

the elementary wave is expressed by means of two parameters r and $\Phi_0$, as:

$$x(t) = x_0 + a_1 h \sin(t, r) + b_1 h \cos(t, r)$$

wherein $a_1 = x_1 \cos(\Phi_0)$ and $b_1 = -x_1 \sin(\Phi_0)$, the h sin and h cos functions being defined by:

$$h\cos: (t, r) \to \frac{(1 + r^2)\cos(t) + 2r}{1 + r^2 - 2r\cos(t)}$$

and $$h\sin: (t, r) \to \frac{(1 - r^2)\sin(t)}{1 + r^2 - 2r\cos(t)};$$

the phase equation is expressed as:

$$F(\Phi) = \frac{P(\Phi)}{Q(\Phi)},$$

wherein $P(\Phi)$ and $Q(\Phi)$ are trigonometric polynomials.

the expression of the phase $\Phi(t)$ is determined as:

$$t(\Phi) = \Phi + \sum_{k=1}^{n} a_k p\sin_1(\Phi - p_k, r_k) - b_k p\cos_1(\Phi - p_k, r_k)$$

wherein the $p \sin_1$ and $p \cos_1$ functions are defined by:

$$p\cos_1(t, r) = \sum_{k=1}^{\infty} \cos(kt)\frac{r^k}{k} \text{ and } p\sin_1(t, r) = \sum_{k=1}^{\infty} \sin(kt)\frac{r^k}{k}$$

The thereby achieved method according to the invention allows analysis of ECG signals and characterization of the signals by means of a small number of parameters, as compared with decomposition methods according to the state of the art. Further, these parameters have a physical meaning, and are characteristics of the wave shapes of the PQRST complexes.

According to another aspect, the object of the invention is also a system for analysing the heart activity of a patient, comprising means for acquiring at least one electric cardiac signal comprising at least one elementary signal corresponding to a heart beat, means for extracting from said elementary signal at least one elementary wave, the general shape of which may be expressed as $x(t) = x_0 + x_1 \cos(\Phi(t))$, wherein $\Phi(t)$ is the phase of said elementary wave, and means for analyzing said elementary wave, characterized in that the means for analyzing said elementary wave comprise:

means for determining an expression of a phase equation $$F(\Phi) = \frac{d\Phi}{dt}$$

of said elementary wave; and means for determining an expression of the phase $\Phi(t)$ of said elementary wave depending on parameters measuring the anharmonicity of said elementary wave and its morphology, from $p \cos_n$ and $p \sin_n$ functions defined by:

$$p\cos_n(t, r) = \sum_{k=1}^{\infty} \cos(kt)\frac{r^k}{k^n} \text{ and } p\sin_n(t, r) = \sum_{k=1}^{\infty} \sin(kt)\frac{r^k}{k^n}.$$

The system according to the invention also includes the following characteristics, taken separately or as a combination:

the analysis system includes means for expressing the phase equation as:

$$\frac{d\Phi}{dt} = \frac{1 + r^2 + 2r\cos(\Phi)}{1 - r^2},$$

wherein r, varying in [0,1], is a parameter measuring the anharmonicity of said elementary wave;

the analysis system includes means for expressing the elementary wave by means of two parameters r and $\Phi_0$, as:

$$x(t) = x_0 + a_1 h \sin(t, r) + b_1 h \cos(t, r)$$

wherein $a_1 = x_1 \cos(\Phi_0)$ and $b_1 = -x_1 \sin(\Phi_0)$, the h sin and h cos functions being defined by:

$$h\cos: (t, r) \to \frac{(1 + r^2)\cos(t) + 2r}{1 + r^2 - 2r\cos(t)}$$

and $$h\sin: (t, r) \to \frac{(1 - r^2)\sin(t)}{1 + r^2 - 2r\cos(t)};$$

the analysis system includes means for expressing the phase equation as:

$$F(\Phi) = \frac{P(\Phi)}{Q(\Phi)},$$

wherein $P(\Phi)$ and $Q(\Phi)$ are trigonometric polynomials;

the analysis system includes means for expressing the phase Φ(t) as:

$$t(\Phi) = \Phi + \sum_{k=1}^{n} a_k p\sin_1(\Phi - p_k, r_k) - b_k p\cos_1(\Phi - p_k, r_k)$$

wherein the p $\sin_1$ and p $\cos_1$ functions are defined by:

$$p\cos_1(t, r) = \sum_{k=1}^{\infty} \cos(kt)\frac{r^k}{k} \text{ and } p\sin_1(t, r) = \sum_{k=1}^{\infty} \sin(kt)\frac{r^k}{k}.$$

According to other aspects, the object of the invention is also a cardiac stimulator comprising a system for analyzing heart activity according to the invention, and a cardiac defibrillator comprising a system for analyzing heart activity according to the invention.

Figure 2:
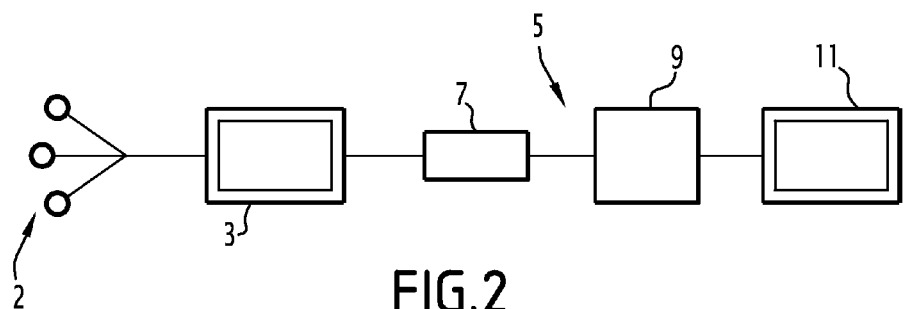
Figure 3:
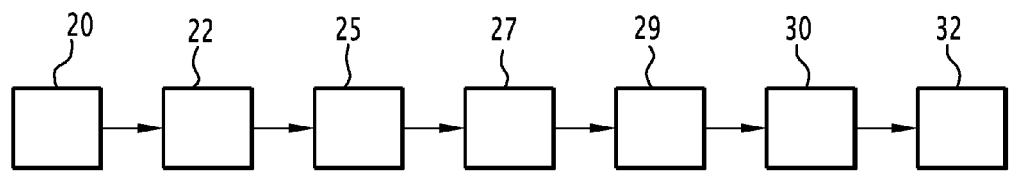

The invention will be better understood with reference to an exemplary embodiment of the invention which will now be described with reference to the appended figures wherein:

FIG. 1 illustrates a PQRST complex of an ECG signal;

FIG. 2 schematically illustrates the system according to an embodiment of the invention; and FIG. 3 is a block diagram illustrating the method according to an embodiment of the invention.

On FIG. 1 a plot is illustrated, which shows the shape of an elementary signal 1 of an ECG signal, comprising a PQRST complex. On this plot, time is represented in abscissas and the voltage in ordinates. The P wave, the QRS complex and the T wave generated during a heart beat are recognized on this plot.

A system for acquiring and analyzing cardiac signals is illustrated in FIG. 2.

This system includes means for acquiring ECG signals, comprising a plurality of measurement electrodes 2, placed in different locations of the body of a patient, and connected to an electrocardiographic monitor 3 (also called an ECG monitor).

This system also includes means 5 for processing and analyzing ECG signals, comprising an analog/digital converter 7 and means 9 for analyzing digital signals, for example, a processor. The input of the converter 7 is connected to an output of the ECG monitor 3, and the input of the processor 9 is connected to the output of the converter 7.

Moreover, the system includes a monitor 11, connected to an output of the processor 9.

The measurement electrodes 2 are capable of receiving, when they are placed on the body of the patient, the electric signals generated in the heart, the amplitude of which is of the order of 1 millivolt. With a set of electrodes, it is possible to receive the signals from multiple leads, generally six or twelve in number.

The ECG monitor 3, is capable of displaying the ECG signals, during their gradual acquisition by the electrodes 1, as curves representing time in abscissas, for example with a scale of 25 mm/s, and voltage in ordinates, for example with a scale of 1 cm/mV. These curves are quasi-periodic, each period corresponding to a heart beat, and their shape is variable according to the relevant lead. FIG. 1 thus illustrates the shape of the signal from one of these leads, over a period corresponding to a heart beat.

The monitor 3 is also capable of delivering at the output, analog signals, corresponding to the ECG signals sensed by the electrodes.

The analog/digital converter 7, is capable of digitizing an analog ECG signal by sampling this signal with a predetermined sampling frequency, for example 256 Hz.

The processor 9 is capable of filtering a digital ECG signal, of analyzing this signal so as to extract therefrom characteristic parameters of the shape of this signal and of the heart rate, and to produce a synthesis of these parameters.

FIG. 3 is a block diagram illustrating the acquisition and the analysis of a cardiac activity signal by means of the system described with reference to FIG. 2, according to an embodiment of the invention.

In a first acquisition step 20, the electric signals generated by the cardiac activity are sensed by the electrodes 2 and transmitted to the ECG monitor 3, as analog signals. The ECG monitor 3 displays, gradually during their reception, several curves illustrating these signals. With this display, it is notably possible for a practitioner to make sure that the signals have been properly acquired.

The signals sensed by the electrodes 2 are for example twelve in number, each of these signals corresponding to a particular lead. With the method according to the invention, it is possible to analyze each of these leads, but only the analysis of a single one of these leads will be detailed subsequently in the description. Thus, subsequently in the description, <<ECG signal>> will designate a signal associated with one of these leads.

In a digitization step 22, the ECG monitor 3 transmits the analog ECG signal to the analog/digital converter 7, which digitizes this signal, by sampling and quantification.

The digital ECG signal obtained at the end of step 22 is transmitted to the processor 9, which analyzes this signal in order to extract characteristic parameters therefrom.

This signal consists of a succession of elementary signals 1, each corresponding to a heart beat, and forming a PQRST complex. However, it is not strictly periodic, notably because of the variability of the heart rate and of the shape of the QRS complex. Moreover, this signal is not due to the sole electric activity of the heart. Indeed, the activity of muscles other than heart muscles, notably respiratory muscles, and the interferences of electric apparatuses, for example, the monitors 3 and 11, generate parasitic signals of high and low frequencies which are also received by the electrodes 2.

Thus, in step 25, digital filtering is applied to the digital ECG signal, so as to suppress these parasitic signals.

In step 27, the filtered ECG signal is broken down into elementary signals Y(t), each comprising a PQRST complex, by means of known methods, for example by detecting the R wave, which is generally the finest and most extensive wave of the PQRST complex. During this decomposition, the heart rate and its variability are determined by calculating the different time intervals separating the successive P waves of the signal.

And the processor 9 then analyzes each of the elementary signals Y(t), and in particular, the morphology of the PQRST complexes.

For this purpose, each elementary signal is analyzed and broken down in a step 29 into a sum of elementary waves, each corresponding to a P, Q, R, S or T wave of the elementary signal Y(t).

Each elementary signal Y(t) is thus described by:

$$Y(t) = x_P(t-t_P) + x_Q(t-t_Q) + x_R(t-t_R) + x_S(t-t_S) + x_T(t-t_T)$$

wherein $x_P$, $x_Q$, $x_R$, $x_S$ and $x_T$ designate the P, Q, R, S and T waves, respectively, and $t_P$, $t_Q$, $t_R$, $t_S$ and $t_T$ designate the time origins of these waves, i.e. the instants at which these waves appear in the elementary signal.

Each of the elementary waves is then analyzed in a step 30, and characterized by a small number of parameters. The analysis of each of these waves is carried out according to the same steps. Thus, subsequently in the description, and elementary wave, regardless of its type, will be designated by x(t), and it will be assumed that its time origin is the instant t=0.

Each elementary wave x(t) is an anharmonic signal which may be described in the following form:

$$x(t)=x_0+x_1\cos(\Phi(t)) \quad (1)$$

wherein all the time dependence is contained in the phase function Φ.

This elementary wave x(t) is considered as a periodic signal of period T, T. Being the period of the locally measured heart rate. Subsequently in the description, a normalized period of value 2π will be considered.

In an anharmonic signal, the main contribution to anharmonicity comes from the breaking of symmetry of the phase dynamics. Thus, or all the relevant dynamic information is expressed by the phase dynamics. Early during the analysis of the wave x(t), this phase Φ(t) should therefore be studied, and in particular the phase dynamics expressed by the function F, the time derivative of function Φ:

$$F(\Phi) = \frac{d\Phi}{dt} \quad (2)$$

Thus, the morphology of the wave x(t) is completely determined by knowing F.

During the analysis step 30 of the method according to the invention, this function F should therefore be described by means of a very small number of parameters. By a small number of parameters, will be meant a reduced number of parameters relatively to the number of parameters required for breaking down the same function, by means of Fourier series, with an equivalent accuracy level.

This analysis step 30 thus comprises a first step consisting of expressing the phase Φ, And in particular the function F, the time derivative of Φ.

In the simplest case, and for a wave of period 2π, The phase dynamics may be written as:

$$F(\Phi) = \frac{d\Phi}{dt} = \frac{1+r^2+2r\cos(\Phi)}{1-r^2} \quad (3)$$

called a phase equation.

The function F in this case has a reflection symmetry with respect to the axis Φ=0. This expression of the phase dynamics only contains a single parameter, r, which varies in the interval [0,1]. The limit r=0 corresponds to a harmonic wave, the limit r=1 to an infinitely anharmonic wave.

The wave x(t), which may be written as:

$$x(t)=x_0+x_1\cos(\Phi(t,r)-\Phi_0) \quad (4)$$

wherein $\Phi_0$ is a phase origin, is broken down and rewritten in a form involving parameters r and $\Phi_0$ $$x(t)=x_0+a_1 h\sin(t,r)+b_1 h\cos(t,r) \quad (5)$$

with $a_1=x_1\cos(\Phi_0)$ and $b_1=-x_1\sin(\Phi_0)$, and in which are defined the following h cos and h sin functions:

$$h\cos: (t, r) \to \frac{(1+r^2)\cos(t)+2r}{1+r^2-2r\cos(t)} \quad (6)$$

$$h\sin: (t, r) \to \frac{(1-r^2)\sin(t)}{1+r^2-2r\cos(t)} \quad (7)$$

Thus, the breaking down of the wave x(t) only involves two parameters r and $\Phi_0$.

r, called an anharmonicity parameter, measures the anharmonicity degree of the wave, the limit r=0 corresponds to a harmonic wave, the limit r=1 to an infinitely anharmonic wave. Moreover, the parameter $\Phi_0$, which defines the composition of the wave in both functions h cos and h sin, is a morphology parameter, which corresponds to the angle of reflection symmetry of the phase dynamics.

In the general case, i.e. for any periodic wave, the phase equation may be written as:

$$F(\Phi) = \frac{P_n(\Phi)}{Q_m(\Phi)} \quad (8)$$

wherein $P_n$ and $Q_m$ are trigonometric polynomials of respective degrees n and m. The general shape of a trigonometric polynomial of degree n is:

$$P_n(\Phi) = a_0 + \sum_{k=1}^{n} a_k \cos(k\Phi) + b_k \sin(k\Phi) \quad (9)$$

The analysis of the wave x(t) therefore comprises the determination of an expression of Φ Involving a small number of parameters, which allows determination of an expression of the wave x(t), depending on these parameters.

Advantageously, the phase equation (2) may be rewritten as:

$$\frac{1}{F(\Phi)} = \frac{dt}{d\Phi} = \frac{Q_m(\Phi)}{P_n(\Phi)} \quad (10)$$

By factorizing out the polynomial $P_n(\Phi)$, it is possible to transform $$\frac{1}{F(\Phi)}$$

into a sum of simple terms, which allows the phase equation to be rewritten as:

$$\frac{dt}{d\Phi} = a_0 + \sum_{k=1}^{n} \frac{a_k\cos(\Phi-p_k)+b_k\sin(\Phi+p_k)}{(1+r_k^2-2r_k\cos(\Phi+p_k))} \quad (11)$$

wherein the parameters $r_k$, comprised between 0 and 1, measure the anharmonic city of the wave x(t), and the parameters $p_k$ characterize its morphology.

The period T of the wave may be determined by integrating this equation relatively to $\Phi$, between 0 and $2\pi$:

$$T = \int_{\Phi=0}^{\Phi=2\pi} \frac{d\Phi}{F(\Phi)} = 2\pi\left(a_0 + \sum_k \frac{r_k a_k}{1 - r_k^2}\right) \quad (12)$$

From this results, and from constraints according to which the period is equal to $2\pi$, and the wave is harmonic when the coefficients $r_k$ are all zero, the phase equation may be expressed in the following way:

$$\frac{dt}{d\Phi} = 1 + \sum_{k=1}^{n} D_k(\Phi - p_k) \quad (13)$$

wherein the function $D_k$ is defined by:

$$D_k: \Phi \to \frac{r_k(a_k\cos(\Phi) + b_k\sin(\Phi) - a_k)}{(1 + r_k^2 - 2r_k\cos(\Phi))} \quad (14)$$

and verifies:

$$\int_{\Phi=0}^{\Phi=2\pi} D_k(\Phi) d\Phi = 0 \quad (15)$$

The definition of the poly cos and poly sin functions, noted as $p\cos_n$ and $p\sin_n$, which are expressed by:

$$p\cos_n(t, r) = \sum_{k=1}^{\infty} \cos(kt)\frac{r^k}{k^n} \quad (16)$$

$$p\sin_n(t, r) = \sum_{k=1}^{\infty} \sin(kt)\frac{r^k}{k^n} \quad (17)$$

and inter alia have the following properties:

$$p\cos_0(t, r) = \frac{r(\cos(t) - r)}{1 + r^2 - 2r\cos(t)} \quad (18)$$

$$p\sin_0(t, r) = \frac{r\sin(t)}{1 + r^2 - 2r\cos(t)} \quad (19)$$

$$p\cos_1(t, r) = -\frac{1}{2}\ln(1 + r^2 - 2r\cos(t)) \quad (20)$$

$$p\sin_1(t, r) = \tan^{-1}\left(\frac{r\sin(t)}{1 - r\cos(t)}\right) \quad (21)$$

allows the phase equation to be rewritten as:

$$\frac{dt}{d\Phi} = 1 + \sum_{k=1}^{n} a_k p\cos_0(\Phi - p_k, r_k) + b_k p\sin_0(\Phi - p_k, r_k) \quad (22)$$

By solving this equation, it is possible to access an analytical expression of $t(\Phi)$, Which is expressed by:

$$t(\Phi) = \Phi + \sum_{k=1}^{n} a_k p\sin_1(\Phi - p_k, r_k) - b_k p\cos_1(\Phi - p_k, r_k) \quad (23)$$

The time t is therefore expressed as a function of the phase $\Phi$, and in a dual way the phase $\Phi$ Is expressed as a function of time t, by means of clearly defined independent parameters, which measure the anharmonicity (parameters r or $r_k$), and the morphology (parameters $\Phi_0$ or $p_k$).

Thus, during the analysis step 30, the processor 9 encodes each elementary wave x(t) by means of a small number of parameters. According to an embodiment, each elementary wave x(t) is described in an almost exact way by an amplitude, a harmonicity r and a morphology $\Phi_0$. According to another embodiment, each elementary wave x(t) is even more accurately described by two pairs of parameters $(r_1, p_1)$ and $(r_2, p_2)$, completed with their respective weights.

Each of the elementary wave is, therefore each of the PQRST complexes, of the ECG signal, is therefore characterized by a restricted number of parameters, bearing a physical meaning since they are representative of the non-linearity and of the morphology of these complexes.

In a step 32, the processor 9 synthesizes the parameters of the ECG signal determined during steps 27 and 29, i.e. the heart rate and the harmonicity and morphology parameters, notably by determining the average and the standard deviation of each of these parameters on the whole of the ECG signal. These values are displayed on the monitor 11, and may be used as a basis for a diagnosis, by a practitioner or automatically, by comparing these values, with tabulated values corresponding to a particular heart abnormalities.

With the method according to the invention, it is thus possible to analyze a cardiac activity and to extract from electric signals generated by the cardiac activity, a restricted number of parameters allowing a compact and relevant representation of the waveform of these signals.

However, it should be understood that the exemplary embodiment shown above is non-limiting.

Notably, according to another embodiment, the cardiac activity signal is an electrogram, collected by electrodes placed on endocavitary probes.

The system man the method according to the invention may thus be applied in an implanted stimulator or defibrillator, continuous analysis of the cardiac activity signals according to the invention, allowing automatic detection of potential abnormalities, and triggering of a stimulation of the heart.

Of course, other embodiments may be envisioned.

The invention claimed is:

1. A system for analyzing the cardiac activity of a patient comprising means (2) for acquiring at least one cardiac electric signal comprising at least one elementary signal (1) corresponding to a heart beat, means for extracting from said elementary signal (1), at least one elementary wave (P, Q, R, S, T), the general shape of which may be expressed by x(t)= $x_0+x_1 \cos(\Phi(t))$, wherein $\Phi(t)$ is the phase of said elementary wave (P, Q, R, S, T), and means (9) for analyzing said elementary wave (P, Q, R, S, T), characterized in that the means (9) for analyzing said elementary wave (P, Q, R, S, T) comprise:

means (9) for determining an expression of a phase equation $$F(\Phi) = \frac{d\Phi}{dt}$$

of said elementary wave (P, Q, R, S, T); and means (9) for determining an expression of the phase $\Phi(t)$ of said elementary wave (P, Q, R, S, T) as a function of parameters ($r, r_k, \Phi_0, p_k$) measuring the anharmonicity of said elementary wave (P, Q, R, S, T) and its morphology, from p $\cos_n$ and p $\sin_n$ functions defined by:

$$p\cos_n(t, r) = \sum_{k=1}^{\infty} \cos(kt)\frac{r^k}{k^n} \text{ and } p\sin_n(t, r) = \sum_{k=1}^{\infty} \sin(kt)\frac{r^k}{k^n}.$$

2. The system for analyzing cardiac activity according to claim 1, characterized in that it includes means (9) for expressing the phase equation as:

$$\frac{d\Phi}{dt} = \frac{1 + r^2 + 2r\cos(\Phi)}{1 - r^2},$$

wherein r, varying in [0,1], is a parameter measuring the anharmonicity of said elementary wave (P, Q, R, S, T).

3. The system for analyzing cardiac activity according to claim 2, characterized in that it includes means (9) for expressing the elementary wave x(t) by means of two parameters r and $\Phi_0$, as:

$$x(t)=x_0+a_1 h \sin(t,r)+b_1 h \cos(t,r)$$

wherein $a_1=x_1 \cos(\Phi_0)$ and $b_1=-x_1 \sin(\Phi_0)$, the h sin and h cos functions being defined by:

$$h\cos: (t, r) \to \frac{(1 + r^2)\cos(t) + 2r}{1 + r^2 - 2r\cos(t)} \text{ and}$$

$$h\sin: (t, r) \to \frac{(1 - r^2)\sin(t)}{1 + r^2 - 2r\cos(t)}.$$

4. The system for analyzing cardiac activity according to claim 3, characterized in that it includes means (9) for expressing the phase equation as:

$$F(\Phi) = \frac{P(\Phi)}{Q(\Phi)},$$

wherein $P(\Phi)$ and $Q(\Phi)$ are trigonometric polynomials.

5. The system for analyzing cardiac activity according to claim 4, characterized in that it includes means (9) for expressing the phase $\Phi(t)$ as:

$$t(\Phi) = \Phi + \sum_{k=1}^{n} a_k\, p\sin_1(\Phi - p_k, r_k) - b_k\, p\cos_1(\Phi - p_k, r_k)$$

wherein the p $\sin_1$ and p $\cos_1$ functions are defined by:

$$p\cos_1(t, r) = \sum_{k=1}^{\infty} \cos(kt)\frac{r^k}{k} \text{ and } p\sin_1(t, r) = \sum_{k=1}^{\infty} \sin(kt)\frac{r^k}{k}.$$

6. A cardiac stimulator comprising a system for analyzing cardiac activity according to one of claims 1 to 5.

7. A cardiac defibrillator comprising a system for analyzing cardiac activity according to one of claims 1 to 5.

* * * * *